United States Patent
Brown (10) Patent No.: US 12,352,837 B2
(45) Date of Patent: Jul. 8, 2025

(54) PSEUDO-CT IMAGE GENERATION

(71) Applicant: Elekta Limited, Crawley (GB)

(72) Inventor: Kevin Brown, Crawley (GB)

(73) Assignee: Elekta Limited, Crawley (GB)

( * ) Notice: Subject to any disclaimer, the term of this patent is extended or adjusted under 35 U.S.C. 154(b) by 648 days.

(21) Appl. No.: 17/753,238

(22) PCT Filed: Aug. 27, 2020

(86) PCT No.: PCT/EP2020/074011
§ 371 (c)(1),
(2) Date: Feb. 24, 2022

(87) PCT Pub. No.: WO2021/038002
PCT Pub. Date: Mar. 4, 2021

(65) Prior Publication Data
US 2022/0291318 A1     Sep. 15, 2022

(30) Foreign Application Priority Data
Aug. 30, 2019 (GB) .................... 1912529

(51) Int. Cl.
| | |
|---|---|
| *G01R 33/56* | (2006.01) |
| *A61B 6/00* | (2024.01) |
| *A61B 6/03* | (2006.01) |
| *A61N 5/10* | (2006.01) |
| *G01R 33/54* | (2006.01) |
| *G06T 7/00* | (2017.01) |

(52) U.S. Cl.
CPC .......... *G01R 33/5608* (2013.01); *A61B 6/03* (2013.01); *A61B 6/5235* (2013.01); *G01R 33/543* (2013.01); *G06T 7/0012* (2013.01); *G06T 2207/30096* (2013.01)

(58) Field of Classification Search
CPC ...... G01R 33/5608; A61B 6/03; A61B 6/5235
See application file for complete search history.

(56) References Cited

U.S. PATENT DOCUMENTS

| | | | |
|---|---|---|---|
| 2019/0015060 A1* | 1/2019 | Weiss | A61B 5/055 |
| 2019/0209099 A1* | 7/2019 | Han | G16H 30/20 |
| 2019/0304145 A1 | 10/2019 | Lin et al. | |

FOREIGN PATENT DOCUMENTS

| | | |
|---|---|---|
| CN | 101005874 | 7/2007 |
| EP | 2369551 A1 | 9/2011 |
| EP | 3426342 A1 | 1/2019 |

(Continued)

OTHER PUBLICATIONS

"International Application Serial No. PCT/EP2020/074011, International Search Report dated Nov. 17, 2020", (Nov. 17, 2020), 5 pgs.

(Continued)

*Primary Examiner* — Colin T. Sakamoto
(74) *Attorney, Agent, or Firm* — Schwegman Lundberg & Woessner, P.A.

(57) ABSTRACT

Disclosed herein is a method for producing a calibrated pseudo-CT image of at least part of a patient for radiation treatment planning. The method comprises obtaining radiation intensity data indicative of attenuation properties of tissues within the patient and calibrating a first pseudo-CT image of at least part of the patient using the radiation intensity data to produce the calibrated pseudo-CT image.

20 Claims, 6 Drawing Sheets

(56) References Cited

FOREIGN PATENT DOCUMENTS

WO  WO-2015081079 A1  6/2015
WO  WO-2015103184 A1  7/2015

OTHER PUBLICATIONS

"International Application Serial No. PCT/EP2020/074011, Written Opinion dated Nov. 17, 2020", (Nov. 17, 2020), 7 pgs.
"United Kingdom Application Serial No. 1912529.3, Examination Report dated Feb. 24, 2020", (Feb. 24, 2020), 8 pgs.
Burgos, Ninon, et al., "Robust CT synthesis for radiotherapy planning: application to the head and neck region", International Conference on Medical Image Computing and Computer-Assisted Intervention. Springer, Cham, (2015), pp. 476-484.
"Chinese Application No. 202080059900.7, Office Action dated May 17, 2025", w English Translation, (May 17, 2025), 12 pgs.

\* cited by examiner

PSEUDO-CT IMAGE GENERATION

PRIORITY APPLICATIONS

This application is a U.S. National Stage Filing under 35 U.S.C. § 371 from International Application No. PCT/EP2020/074011, filed on Aug. 27, 2020, and published as WO2021/038002 on Mar. 4, 2021, which claims the benefit of priority to United Kingdom Application No. 1912529.3, filed on Aug. 30, 2019; the benefit of priority of each of which is hereby claimed herein, and which applications and publication are hereby incorporated herein by reference in their entireties.

This disclosure relates to radiotherapy techniques, and in particular to a system and method for producing a calibrated pseudo-CT image of at least part of a subject suitable for use in radiation treatment planning.

BACKGROUND

Radiotherapy can be described as the use of ionising radiation, such as X-rays, to treat a human or animal body. Commonly, radiotherapy is used to treat tumours within the body of a patient or subject. In such treatments, ionising radiation is used to irradiate, and thus destroy or damage, cells which form part of the tumour. However, in order to apply a prescribed dose to a tumour or other target region within a subject, the radiation must pass through healthy tissue, irradiating and hence potentially damaging it in the process. It is a general aim of the field to minimise the dose received by healthy tissue during radiotherapy treatments.

Many different radiotherapy techniques exist, allowing radiation to be applied from different angles, at varying intensities, and for specific time periods. Before radiotherapy treatment, a radiation therapy treatment plan is created to determine how and where the radiation should be applied. Typically, such a treatment plan is created with the assistance of medical imaging technology. For example, a CT scan may be taken of the patient in order to produce a three-dimensional image of the area to be treated. The three-dimensional image allows the treatment planner to observe and analyse the target region and identify surrounding tissues.

Different structures within the body of the patient, for example bone, lung, muscle, etc., will attenuate and absorb radiation to differing degrees based on their respective densities. In other words, different tissues within the human body have different radiodensities, and hence attenuate and/or absorb radiation to differing degrees. Bone is an example of a particularly radiodense or radiopaque tissue. In contrast, soft tissue, for example lung tissue, is radiolucent. The radiodensity of various tissues can be quantified using, for example, the Hounsfield scale in a manner which is known to the skilled person. In order to plan the radiotherapy treatment, it is necessary to obtain information regarding the radiodensity of not only the target region but also surrounding tissues and any regions of the body through which the radiation treatment beam will pass.

Traditionally, the patient is given a CT scan prior to treatment, which not only provides information about the patient geometry via a three-dimensional image of the patient, but also provides information regarding the radiodensities of the different tissues and structure within the patient's body. A CT scan typically produces a three-dimensional image comprised of voxels, where each voxel is assigned a CT value. Each voxel is associated with a particular location within the patient's body, and the CT-values of the voxels together describe the radiodensity of tissues within the patient's body. The CT-values are determined using CT-scanning techniques and on the CT-values are indicative of the attenuation properties of tissues within the patient's body. CT-values can be expressed in Hounsfield units and are directly related to the electron density information which is needed for radiation dose calculations.

However, a CT scan involves irradiating the patient from a number of angles in order to produce the three-dimensional image. Therefore, a disadvantage of CT scanning is that it adds a radiation dose to the patient even before treatment has started. Also, while CT scans can provide the necessary information regarding tissue densities for radiation treatment planning, CT scans provide poor soft tissue contrast. This makes it difficult for a treatment planner to distinguish between certain kinds of soft tissue. For example, it is very difficult to see a tumour in a prostate CT scan, because the tumour and the prostate have very similar densities and attenuation properties and thus look similar, or even identical, in a CT image.

By comparison, obtaining magnetic resonance (MR) images does not involve exposing a patient to ionising radiation, and hence does not provide any dose to the patient. Instead, MR scanners use magnetic fields to excite atoms, typically hydrogen atoms, to emit a radio frequency signal which may be detected and processed to form a three-dimensional image of the patient. MR images provide good soft tissue contrast, allowing a treatment planner to better distinguish between, for example, tumour tissue and prostate tissue. The disadvantage of MR scanning is that it does not indicate the attenuation properties of tissues within the subject, i.e. the patient's tissue radiodensity information, which is required to create a radiation treatment plan.

It is already possible to combine MR and CT data to facilitate the treatment planning process. It is known that MR images and CT images may be obtained independently and then aligned with each other, for example by aligning various discernible locations of features of interest in both images. Such alignment, or fusing, may involve either rigid or deformable adjustment of the MR image to align with the CT image to produce a pair of co-aligned images. However, such alignment, or registration, always has an associated uncertainty or error.

A certain degree of progress in the field has been made by creating so-called 'pseudo-CT' images. Pseudo-CT images are images similar to those obtained from a CT scan, i.e. which comprise tissue radiodensity information, but which are derived primarily or entirely from MR data such as an MR image of the patient.

One way of producing a pseudo-CT image involves making use of previous scan data and 'atlas' images. In a typical technique which makes use of atlas images, multiple CT/MR image pairs from previous scans, either all of the same patient, or of various patients, are co-registered. An 'average' MR image is created by combining each MR image from each co-registered pair. By analysing the deformations required to deform the MR image of a particular pair of MR/CT images in order to reach the average MR atlas image and applying those same deformations to the corresponding CT image of the pair, multiple deformed CT images can be produced. This allows an 'average' CT image to be produced. This is an average CT atlas image. The average MR atlas image and the average CT atlas image together provide a mapping, which describes how new MR images should be deformed in order to produce a pseudo-CT image. For example, a new MR image can be registered to the average MR atlas image. The deformations required for this registration may be applied to the pre-existing average CT atlas image. This produces a so-called pseudo-CT image, which has been derived from previous scan data (of other patients) and new MR images (of the patient to be treated). Notably, no new CT scan data is required and thus the patient to be treated is not given any radiation dose during the imaging process.

Techniques based on previous scans or training data can provide serviceable pseudo-CT images. However, as the pseudo-CT values in the resulting pseudo-CT images are based on averages taken from multiple previous CT and MRI scans, the voxel CT-values in any resulting pseudo-CT image are inherently inaccurate. If the pseudo-CT image contains voxels having pseudo-CT values which are, for example, on average 5% wrong, this can have a significant impact on the treatment planning, and can result in the patient receiving a larger dose of radiation than is required.

Many current pseudo-CT techniques use data taken from a database of previous scans in a manner similar to the method described above, however the previous scans often do not use the same scanning techniques or equipment as is used to obtain the new, 'input' MR image. The previous data used to produce the pseudo-CT image is often also taken from a range of different patients at various different times. These factors, and others, introduce errors into the calculation of pseudo-CT values and hence any treatment plan based on the pseudo-CT image may not be fully optimal. Also, currently known methods may involve taking an MRI scan for the purpose of producing a pseudo-CT image, and may then involve performing the actual radiotherapy treatment at a later time, allowing the patient to move, sometimes significantly, between scanning and treatment positions. A patient's organs are not entirely static within the body, and can move slightly between scan and treatment, especially over the course of days, weeks or even months between the MRI scan and the radiotherapy treatment. This means that even if the calculated pseudo-CT values are accurate based on the patient's body at the time of the MRI scan, the three-dimensional pseudo-CT image may be less accurate at the time of treatment.

It is an aim of the present disclosure to utilise imaging technologies to provide information upon which to base a treatment plan, whilst minimising the radiation dose to a patient. The present invention seeks to address the above-discussed and other disadvantages encountered in the prior art by providing a method and system for refining, e.g. calibrating, a pseudo-CT image for radiation treatment planning.

SUMMARY

Aspects of the present invention are defined in the accompanying independent claims. Optional features are set out in the dependent claims.

According to an aspect of the disclosure, there is provided a method for producing a calibrated pseudo-CT image of at least part of a patient for radiation treatment planning. The method comprises obtaining radiation intensity data indicative of attenuation properties of tissues within the patient. The method further comprises producing, using the radiation intensity data to calibrate an first pseudo-CT image of at least part of a patient, a calibrated pseudo-CT image.

The pseudo-CT images may be described as a spatial map of estimated electron densities within the subject, with the estimated electron densities being calculated, or determined, based on MR image data. Similarly, the MR data may comprise a spatial map of soft tissue within the subject.

Producing the calibrated pseudo-CT image may be described as calibrating the first pseudo-CT image.

The first pseudo-CT image may have been produced based on MR data, optionally wherein the MR data has been obtained by imaging the patient with an MR imager.

The method may further comprise obtaining the first pseudo-CT image of at least part of the patient, for example by imaging the patient with an MR imager to obtain the MR data or by other means such as obtaining the first pseudo-CT image from a database.

Optionally, the patient may be positioned on a patient support surface while the MR data and radiation intensity data are obtained. The patient support surface may be a single, particular patient support surface, for example the patient support-surface of an MR-linac.

The first pseudo-CT image may be produced based on previously obtained MR data and previously obtained radiation intensity data. The previously obtained MR data and radiation intensity data may comprise MR and CT images of the patient, or of other patients.

The first pseudo-CT image may comprise a plurality of voxels, each respective voxel being associated with a pseudo-CT value, and producing the calibrated pseudo-CT image may comprise comparing the obtained radiation intensity data with estimated radiation intensity data, the estimated radiation intensity data being based on at least one of the pseudo-CT values. The method may comprise updating, based on the comparison, each pseudo-CT value of the first pseudo-CT image to produce the calibrated pseudo-CT image.

The method may further comprise delivering radiation from a radiation source to the patient and obtaining the radiation intensity data from a radiation detector. The obtained radiation intensity data is indicative of the attenuation properties of tissue within the patient, for example the data may be indicative of the degree to which the delivered radiation is attenuated as it passes through the patient.

Delivering the radiation to the patient may further comprise irradiating a target region within the patient's body to deliver a radiation dose to the target region according to a radiotherapy treatment plan, and may further comprise producing the radiotherapy treatment plan based on the first pseudo-CT image.

The method may further comprise delivering a second dose of radiation to the patient to deliver a second radiation dose to the target region according to a second radiotherapy treatment plan, the second radiotherapy treatment plan being based on the calibrated pseudo-CT image.

The method may further comprise delivering radiation to the patient according to a treatment plan and updating the treatment plan a plurality of times in an iterative process, each iteration of the iterative process comprising: delivering radiation to the patient to deliver a dose of radiation to a target region according to the treatment plan; obtaining radiation intensity data indicative of attenuation properties of tissues within the patient; updating the calibrated pseudo-CT image using the radiation intensity data; and updating the treatment plan based on the updated calibrated pseudo-CT image.

Optionally, the radiation intensity data may comprise a calibration CT image of the (at least) part of the patient that is being imaged. The calibration CT image has a lower resolution than the first pseudo-CT image and may be obtained via a process which imparts a lower dose to the patient than a typical clinical CT scan as will be described elsewhere herein.

According to another aspect there is provided a computer readable medium comprising computer-executable instructions which, when executed by a processor, cause the processor to perform any of the methods disclosed herein. The computer readable medium may be a non-transitory computer readable medium.

According to another aspect there is provided a system for producing a calibrated pseudo-CT image of at least part of a patient for radiation treatment planning. The system comprises a radiation source and a radiation detector, the radiation source configured to and suitable for delivering radiation to the patient, and the radiation detector being arranged to detect the intensity of radiation which has passed through the patient. The system also comprises a controller, for example a processor, and a computer readable medium, the computer readable medium comprising computer-executable instructions which, when executed by the controller, cause the system to perform any of the methods disclosed herein. The system may further comprise an MR imager, and may optionally be an MR-linac.

Also disclosed herein is a system for producing a calibrated pseudo-CT image of at least part of a subject for radiation treatment planning. The system comprises a subject support surface, a magnetic resonance (MR) imager for obtaining MR images of a subject positioned on the subject support surface, and a radiation source and a radiation detector, the radiation source for delivering radiation to the subject positioned on the subject support surface, and the radiation detector being arranged to detect the intensity of radiation which has passed through the subject. The system further comprises a controller, and a computer readable medium, the computer readable medium comprising computer-executable instructions which, when executed by the controller, cause the system to perform a method comprising imaging the subject with the MR imager to obtain MR data, producing a pseudo-CT image based on the MR data, delivering radiation from the radiation source to a subject on the subject support surface, obtaining radiation intensity data from the radiation detector, the radiation intensity data being indicative of attenuation properties of tissues within the subject, and producing, using the radiation intensity data to calibrate the pseudo-CT image, a calibrated, i.e. refined, pseudo-CT image.

Also disclosed herein is a method for producing a calibrated pseudo-CT image of at least part of a subject for radiation treatment planning, the method comprising imaging the subject with an MR imager to obtain MR data, producing a pseudo-CT image of at least part of the subject based on the MR data, obtaining radiation intensity data indicative of attenuation properties of tissues within the subject, and producing, using the radiation intensity data to calibrate the pseudo-CT image, a calibrated pseudo-CT image.

FIGURES

Specific embodiments are now described, by way of example only, with reference to the drawings, in which.

DETAILED DESCRIPTION

Figure 1:
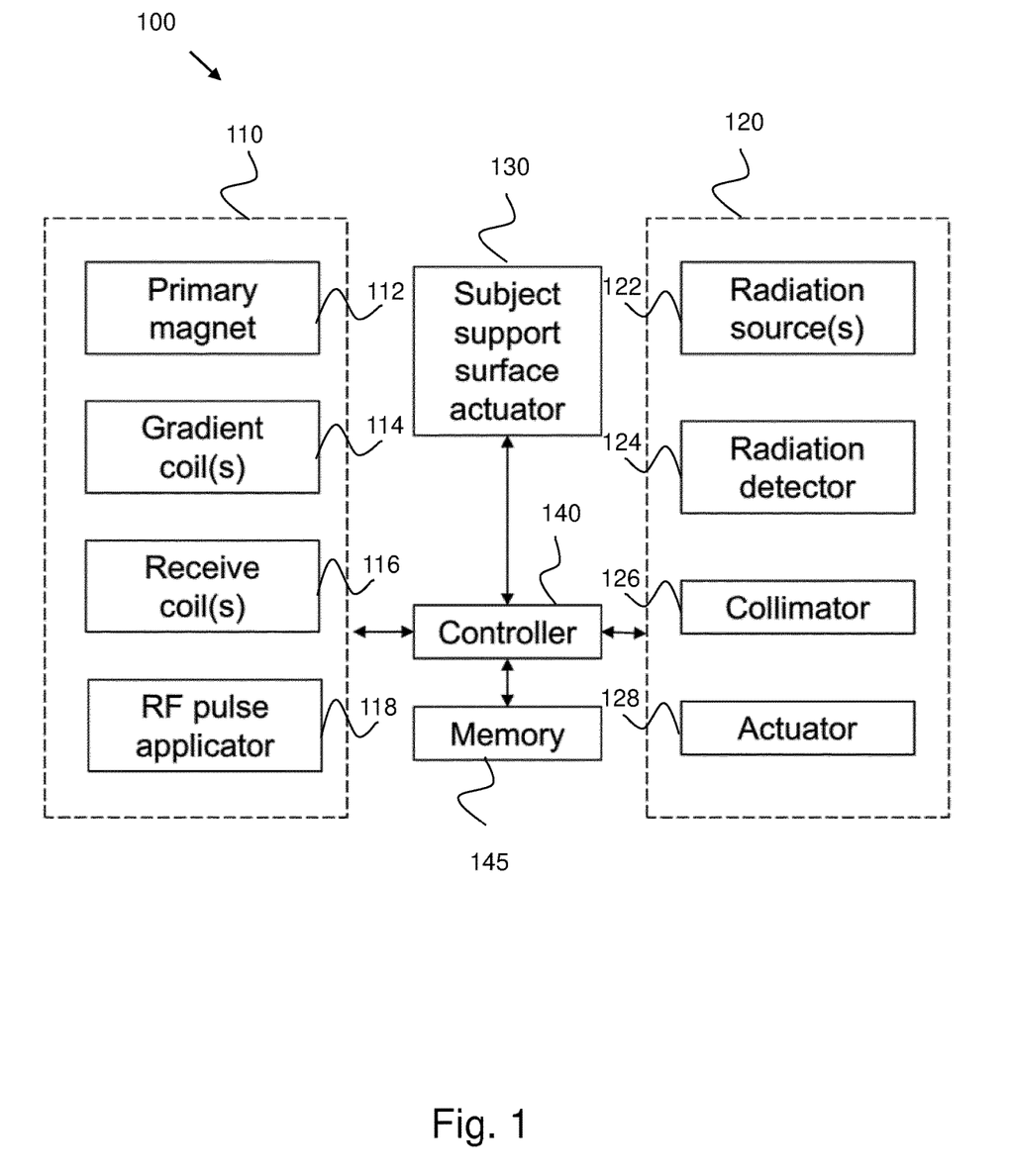
FIG. 1 depicts a system according to the present disclosure.

FIG. 1 depicts a schematic diagram of a system 100, or apparatus, according to the present disclosure. The system is shown by way of example and the skilled person will appreciate that other systems and apparatuses may be equally capable of performing the disclosed methods. The depicted system comprises an MR imaging apparatus 110 and a radiotherapy (RT) apparatus 120. The MR imaging apparatus 110 and radiotherapy apparatus 120 may operate and function in a generally known manner and may together form part of an MR-linac. The system also comprises a housing, a bore, and a moveable support surface which can be used to move a patient, or other subject, into the bore when an MR scan and/or when radiotherapy is to commence. The MR imaging apparatus 110, RT apparatus 120, and a subject support surface actuator 128 are communicatively coupled to a controller or processor 140. The controller 140 is also communicatively coupled to a memory device 145 comprising computer-executable instructions which may be executed by the controller 140 in order to perform the presently disclosed methods.

The subject support surface is configured to move between a first position substantially outside the bore, and a second position substantially inside the bore. In the first position, a patient or subject can mount the patient support surface. The support surface, and patient, can then be moved inside the bore, to the second position, in order for the patient to be imaged by the MR imager 110 and/or imaged or treated using the RT apparatus 120. The support surface can be moved to the second position, inside the bore, at which position methods of the present disclosure may be performed. The movement of the patient support surface is effected and controlled by the subject support surface actuator 128, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The MR imaging apparatus 110 is configured to obtain images of a subject positioned, i.e. located, on the subject support surface. The MR imaging apparatus 110 may also be referred to as the MR imager. The MR imaging apparatus 110 may be a conventional MR imaging apparatus 110 operating in a known manner to obtain MR data, for example. MR images. The skilled person will appreciate that such a MR imaging apparatus 110 may comprise a primary magnet 112, one or more gradient coils 114, one or more receive coils 116, and an RF pulse applicator 118. The operation of the MR imaging apparatus 110 is controlled by the controller.

In an example MR imaging apparatus 110 which may be used in methods of the present disclosure, the primary magnet 112 has coils which are circumjacent to the bore and which are configured to generate a primary magnetic field in accordance with the standard operation of an MR imager/MR imaging apparatus 110. The gradient coils 114 are also positioned circumjacent to the bore such that the coils of the primary magnet 112, the gradient coils 114, and the bore share a common central axis. The gradient coils 114 are positioned and configured to create a magnetic field which has a gradient. Typically, the gradient coils 114 are axially spaced around the bore. The resultant magnetic field has a strength which varies with location, causing hydrogen protons within the patient to interact with the resultant magnetic field in a manner which varies depending on their location. This allows the MRI signal to be spatially encoded. The MR imaging apparatus 110 also comprises a radio frequency (RF) pulse applicator 118, otherwise known as an RF scanner, configured to emit radio frequency pulses at specific frequencies which interact with the hydrogen protons as they precess about the magnetic field. The RF pulses give energy to, i.e. excite, the hydrogen protons, and when the hydrogen protons relax from this excited state, the MR signal is generated. The MR imaging apparatus 110 further comprises receive coils 116, which are configured to receive, i.e. detect, the MR signal. As the protons relax and/or decay from their excited, unaligned state the overall resultant magnetic field is affected. These changes can be detected by the receive coil(s) 116 as induced electric current. This induced current may then be processed according to known techniques to extract frequency and phase information. While reference is made to receive coils 116, in some embodiments the system comprises a radiofrequency system including a single coil that both transmits radio signals and receives the reflected signals. Alternatively, the system may further comprise dedicated transmitting and receiving coils, and/or multi-element phased array coils.

The RT apparatus 120 is configured to direct radiation at the patient. The RT apparatus 120 comprises one or more radiation sources 122 and a radiation detector 124. The RT apparatus 120 further comprises a collimator 126 suitable for, and configured to, collimate radiation emitted by the radiation source(s) 122. The radiation source 122 is suitable for, and configured to, deliver radiation to a patient positioned on the patient support surface. The radiation source(s) 122 may comprise a linear accelerator used to produce a radiation treatment beam. The radiation source(s) 122 may additionally comprise a source of radiation suitable for imaging. The MR imaging apparatus 110 and RT apparatus 120 may together form an MR-linac system.

Typically, the radiation detector 124 is positioned in a manner diametrically opposed to the radiation source 122. The radiation detector 124 is suitable for, and configured to, produce radiation intensity data. In particular, the radiation detector 124 is positioned and configured to detect the intensity of radiation which has passed through the subject. The radiation detector 124 may also be described as a radiation detecting means. The detector may comprise a plurality of component detectors which each measure the intensity of radiation at a particular point on the detector. The RT apparatus 120 may comprise an imaging radiation source 122 and also a different radiation source which may be used for treatment. For example, the apparatus may comprise CBCT apparatus for imaging purposes in addition to a treatment beam. In an example, the radiation detector 124 comprises an imaging panel, e.g. a mega-voltage 'MV' panel, opposite an MV radiation beam source, and the MV panel may be used to image the MV radiation beam after it has passed through the patient.

The RT apparatus 120 further comprises an RT actuator 128, e.g. an actuation mechanism, configured to move the radiation source 122 and radiation detector 124 with respect to the patient support surface. The radiation source 122 and radiation detector 124 are positioned in a manner diametrically opposed to one another to allow the detector to capture and detect radiation emitted by the source. The RT actuation mechanism is configured to rotate the RT mechanism about the bore axis to allow radiation to be delivered to the patient from a variety of different angles in the usual manner. The shape of the beam may vary, and this variation may be controlled, for example, by the collimator 126. The collimator 126 may be a multi-leaf collimator 126 configured to tailor the beam-shape to a particular clinical technique according to the radiation therapy treatment plan.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus 120; and a subject support surface processor which controls the operation and actuation of the subject support surface. The controller is communicatively coupled to a memory, i.e. a computer readable medium. The approaches described herein may be embodied on the computer-readable medium, which may be a non-transitory computer-readable medium. The computer-readable medium may carry computer-readable instructions arranged for execution upon the/a controller so as to make the controller carry out any or all of the methods described herein.

The term "computer-readable medium" as used herein refers to any medium that stores data and/or instructions for causing a processor to operate in a specific manner. Such a storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

Figure 2:
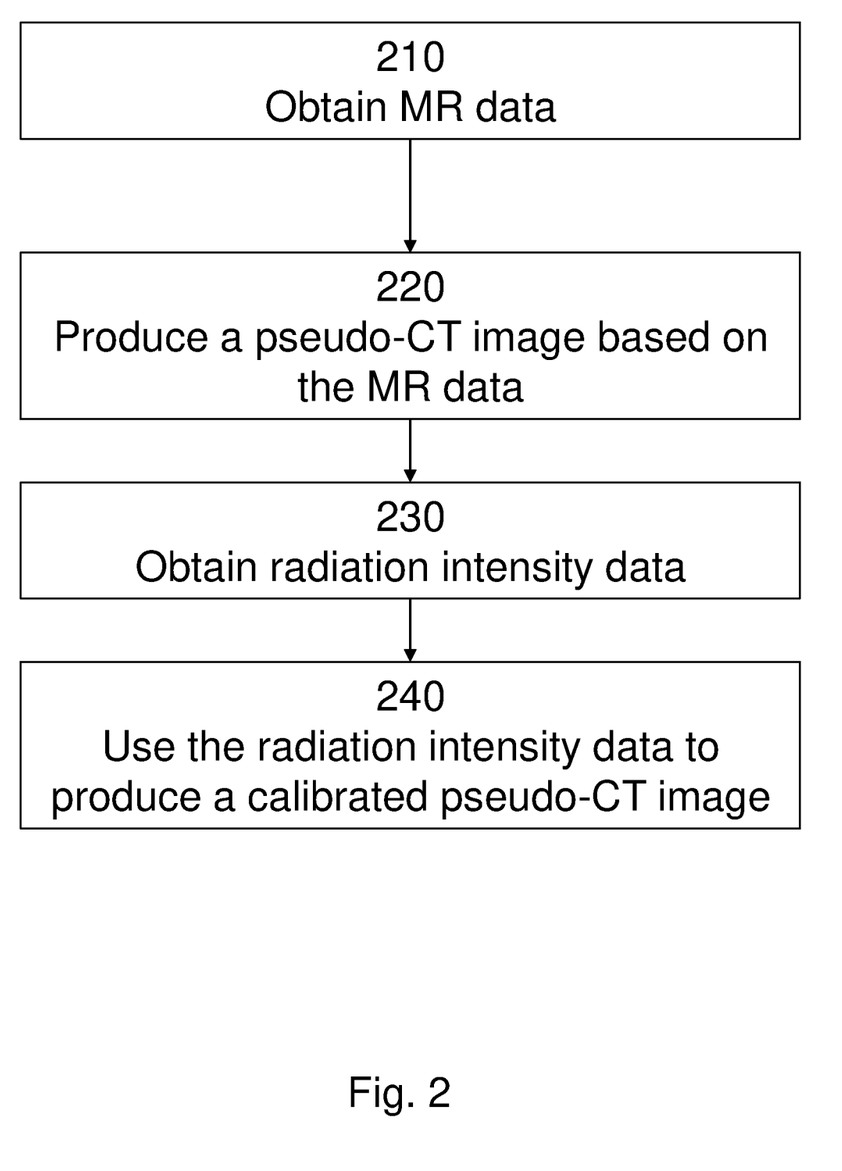
FIG. 2 depicts a flowchart depicting a method of the present disclosure.

FIG. 2 is a flowchart depicting a method according to the present disclosure. The method can be described as a method for producing a refined, e.g. calibrated, pseudo-CT image of at least part of a subject for radiation treatment planning.

At step 210, MR data is obtained. This may involve imaging the subject using an MR imager to obtain the MR data. The MR data is associated with, or comprises, an MR image. In other words, the MR data may be an MR image, or the data may be of a form and type which allows an MR image to be constructed using known techniques. In some implementations of the disclosed method, the MR data is obtained by scanning the patient using an MR imager while the patient is positioned on the patient support surface. MR data can be received by other known methods, for example via email or by retrieving the MR data from the memory following an MR scan of the patient at a different time and/or at a different location.

At step 220, a pseudo-CT image is produced based on the MR data. In other words, a pseudo-CT image is produced using the MR data. The pseudo-CT image may be created using known techniques, for example using bulk density override techniques, voxel-based techniques, and/or atlas-based techniques. The skilled person will be familiar with these techniques, though a non-exhaustive and brief summary of some known methods will be described by way of useful background. Bulk density override techniques are methods of generating a dataset which may be used for dose calculation from an MR image. A bulk density override is applied to the entire patient volume in an MR image. For example, the tissues are separated in the MR image into different categories (e.g. soft tissue, bone, and air) using known segmentation techniques, and every category is assigned an electron density value or a Hounsfield unit (HU) value. In another example, if a region of the MR image is determined to be associated with the patient's liver, each voxel in that region of the image is assigned a particular, predetermined pseudo-CT value. It will therefore be appreciated that bulk density techniques cannot account for any variations in attenuation characteristics within particular tissues.

Voxel-based techniques are an alternative category of methods which may be used to create a pseudo-CT image. In a typical voxel-based technique, the MR intensities of voxels in the MR image are used to assign HU values. These methods typically make use of a pre-determined mapping between MR intensities and HU values. Such a mapping can be created by analysing pairs of co-registered CT and MR images in a database. The MR intensity of a particular voxel in an MR image can be compared with a HU value of a corresponding voxel from the same patient in a CT image. The mapping can be created by comparing co-registered MRI and CT images, and the mapping can be used alongside linear interpolation techniques to allow HU values to be assigned to a three-dimensional grid of voxels based on MR intensities in an MR image to create a pseudo-CT image. Machine-learning techniques are particularly suitable for creating a mapping, if suitable training data (for example a database of co-registered MRI and CT images) is provided.

Figure 3:
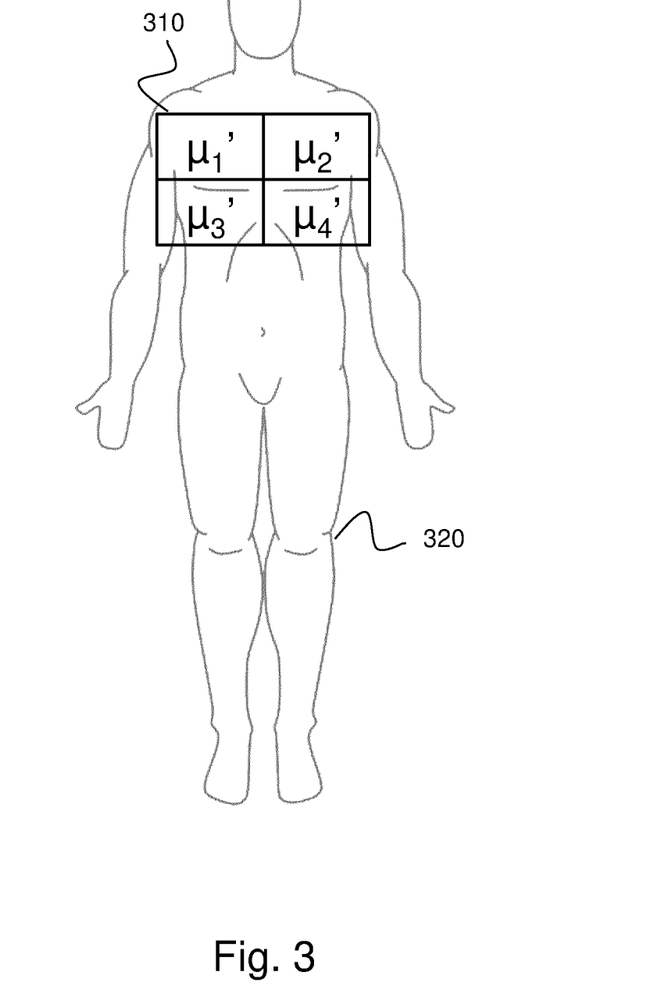
FIG. 3 depicts a pseudo-CT image.

Step 220 of the flowchart of FIG. 2 can be explained by reference to FIG. 3, which shows a simple schematic of a pseudo-CT image 310 of a patient 320. For simplicity, only two dimensions of the pseudo-CT image 310 are depicted in FIG. 3. The pseudo-CT image comprises a plurality of voxels. The voxels form a three-dimensional grid which represents at least a part of the patient's body. As would be appreciated by the skilled person, the voxel size depends on multiple factors, and the voxel size determines the resolution of the pseudo-CT image 310. Each voxel of the pseudo-CT image 310 is associated with a respective pseudo-CT value. Four representative voxels are depicted in the pseudo-CT image 310 of FIG. 3. Each voxel has an assigned pseudo-CT value, depicted in the figure as $\mu_1'$, $\mu_2'$, $\mu_3'$ and $\mu_4'$. Each pseudo-CT value is meant to describe, i.e. be indicative of, the radiodensity of a particular point in the patient's body. The pseudo-CT values are therefore also meant to be indicative of the attenuation properties of tissues within the patient's body.

In other words, each pseudo-CT value is an estimate or an approximation of the CT-value which would be determined if the patient were to undergo a CT scan. However, the determined pseudo-CT values may be inaccurate. Inaccuracies in the determined pseudo-CT values may affect the RT treatment plan. This can cause a higher than required dose of radiation to be prescribed, or a dose of radiation that will not deliver an optimal dose to a tumour.

At step 230 of FIG. 2, radiation intensity data is obtained. The radiation intensity data may be described as transmission data, or radiation transmission data. To obtain the radiation intensity data, the radiation source 122 passes radiation through the patient and the intensity of the radiation after it has passed through the patient is measured in a manner known to the skilled person and described generally elsewhere herein. Finally, at step 240, the radiation intensity data is used to produce a calibrated, or refined, pseudo-CT image. As used herein, refining a pseudo-CT image means creating a new pseudo-CT image which has more accurate pseudo-CT values. Thus, the pseudo-CT image is improved. Another way of thinking about this improvement of the pseudo-CT image is that the pseudo-CT image has been calibrated using the radiation intensity data.

Methods of the present disclosure are advantageous for several reasons. The advantages of existing pseudo-CT techniques are retained. There is no need for a full-CT scan and therefore the overall radiation dose to the patient is reduced. In addition, a more accurate pseudo-CT image is obtained by using pseudo-CT image calibration/refinement techniques in accordance with the presently disclosed methods. A more accurate pseudo-CT image has more accurate pseudo-CT values, and the provision of such a refined pseudo-CT image means that a treatment plan can be made more accurate, in turn ensuring the radiation dose can be better targeted at the target region and the dose to surrounding tissues can be reduced.

The skilled person will appreciate that the steps need not be performed in the order shown in FIG. 2. For example, the order of steps 210 and 230 may be reversed. Alternatively, steps 210 and 230 may be performed at the same time in an appropriately configured system, such as an MR-linac. This is in contrast with prior known methods, in which the MR image, a later CT scan, and then the RT treatment are performed at different times. In prior methods, the imaging and treatment may also be performed on different patient support surfaces according to which machine is being used, e.g. the MR imager, the CT scanner, or the RT apparatus 120. These methods can be problematic, as the distribution of tissues within the patient's body can change significantly between the scans and the treatment. The nature of the tissues may also change. For example, changes in the amount and location of gas in the patient's bowels or fluid in the patient's lungs may cause differences in tissue distribution between the scan and the time of actual treatment. Treatments planned based on images taken at different times and with the patient in different positions can lead to less accurate RT treatment.

In example implementations of the present method, the subject is imaged at step 210, and radiation intensity data is obtained at step 230, while the patient is on the same patient support surface. In other words, the patient is positioned substantially in the same position and substantially with the same tissue geometry while the MR image is obtained and as the radiation intensity data is obtained.

In still further implementations, steps 210 and 230 are performed at the same time. This functionality ensures that the spatial distribution of tissues in the MR image matches the spatial distribution of tissues when the radiation intensity data is obtained. Embodiments in which the MR data and radiation data are obtained substantially at the same time and/or while the patient is in substantially the same position are advantageous because the geometrical characteristics of the resulting images will be more similar, and thus registration of the resulting data and images is facilitated. Also, when the MR data and radiation intensity data are obtained at the same time, it means that each type of data is representative of the patient in a particular geometry, i.e. position, meaning that the effect of conscious or unconscious movement of the patient, which otherwise might introduce inaccuracies into the calibrated pseudo-CT image, can be mitigated.

Embodiments in which the treatment is also performed while the patient is on the same surface are particularly beneficial. In these techniques, the position in which the patient is imaged is the same position in which the patient is treated. Again, these techniques ensure that the images are representative of the geometrical characteristics, e.g. the distribution of tissues, within the patient's body at the time of treatment. This in turn ensures that treatment can be planned more accurately and effectively.

The disclosed methods may therefore further comprise the steps of positioning the subject on the patient support surface while the support surface is in the first position outside the bore and actuating the support surface to a second position inside the bore. Once the patient and support surface are inside the bore, at least steps 210 and 230 of FIG. 2 can be performed. In some embodiments, the MR data and the radiation intensity data is obtained at the same time, or with an overlap in time. After steps 210 and 230 are complete, the support surface is actuated to the first position again, allowing the patient to exit the support surface.

The manner in which the radiation is applied to the patient in step 230 will vary depending on the way in which the pseudo-CT image is to be calibrated at step 240. Numerous implementations are possible and some will be described in detail below.

In a first example implementation of the disclosed method, at step 230 a single instance of radiation is directed at the patient to obtain data which is then used to refine, i.e. calibrate, the pseudo-CT image. The obtained radiation intensity data can be described as normalisation data, or calibration data. In an example, the radiation source 122 is configured to emit a low dose radiation beam such as an MV radiation beam. In this example, a single low dose beam of radiation is passed through the patient and the cumulative MV beam absorption is measured along the path of the beam using the radiation detector 124. The radiation source 122 emits radiation in a single direction and/or at a single projection angle to obtain radiation intensity data indicative of the attenuation properties of tissues in the patient's body. The 'low dose' may be achieved by applying the radiation only for a very short period of time, for example for a length of time significantly shorter than would be used to deliver radiation to a prescribed dose to a target region.

Figure 4:
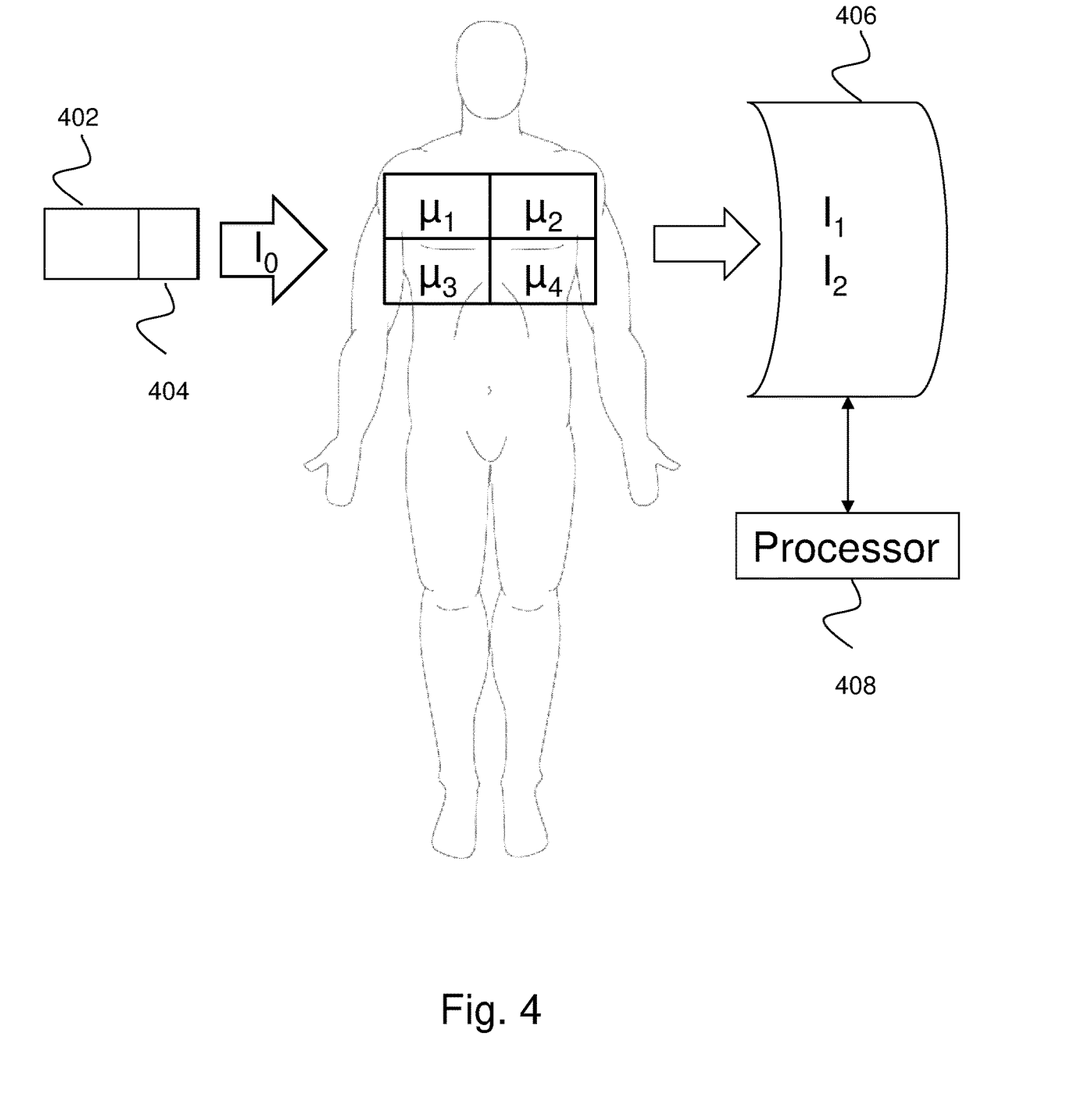
FIG. 4 depicts an implementation of methods of the present disclosure.

FIG. 4 is a simple schematic according to the first implementation. The schematic RT apparatus depicted in FIG. 4 comprises a radiation source 402, a collimator 404, and a detector 406. The radiation source 402 directs radiation in a first direction at the patient, and at a first projection angle with respect to the patient. The radiation may be in the form of a parallel beam of radiation, and/or may be in the form of a cone in an implementation using cone beam computed tomography (CBCT) apparatus. The radiation source 402 emits the radiation with an initial intensity $I_0$, or an initial intensity profile. Typically, the radiation is also emitted at a particular frequency. In other words, the radiation consists of monochromatic photons. In a simple example, the initial beam of radiation may consist of N monochromatic photons emitted per unit time, and the radiation detector 406 may detect N-ΔN photons per unit time. The reduction ΔN in the number of photons is due to attenuation of the radiation within the body of the patient. Thus, radiation data, for example radiation intensity data, is obtained which is indicative of the attenuation properties of tissues within the patient.

As with FIG. 3, only two dimensions are shown in FIG. 4 for simplicity. The different tissues of the patient are represented schematically as simple rectangles with representative attenuation values $\mu_1$, $\mu_2$, $\mu_3$ and $\mu_4$. If the patient were given a full CT-scan, $\mu_1$, $\mu_2$, $\mu_3$ and $\mu_4$ are the CT-values which would be assigned to the depicted areas of the patient's body. The attenuation of the radiation is cumulative as the radiation passes through the different regions of tissue in the patient. The detector 406 measures the intensity of radiation which has passed through the patient and the intensity data is communicated to a controller, or processor, 408.

In this first implementation, at step 240 the obtained radiation intensity data is used to refine the existing pseudo-CT image. With reference to the simplified diagram of FIG. 4, it will be appreciated that the radiation which passes through both regions of tissue with attenuation coefficients $\mu_1$ and $\mu_2$ will be attenuated by an amount dependent on both $\mu_1$ and $\mu_2$. The detected intensity, $I_1$, at the detector can therefore be used along with knowledge of the original intensity $I_0$ of the radiation to determine a cumulative attenuation value which is indicative of $\mu_1+\mu_2$. Similarly, it is possible to determine a cumulative attenuation value which is indicative of $\mu_3+\mu_4$. The cumulative attenuation values are indicative of the beam's reduction in intensity after having passed through the tissue of the patient's body. A plurality of cumulative attenuation values can be determined in this manner, e.g. by directing a beam of radiation in a particular direction through the patient. In other words, a single projection angle is used to obtain cumulative attenuation information. Reference is made to $\mu 1+\mu 2$, i.e. an additive relationship between the coefficients is used. However, the skilled person will appreciate that the particular relationship between the detected radiation intensity I1, original radiation intensity J0, and the attenuation properties of each region of the patient's body will depend on notation and definition used. Regardless of notation, the skilled person will be aware how to produce a standard CT image.

The cumulative attenuation information obtained from the radiation intensity data can be compared to the pseudo-CT values of the pseudo-CT image. As an illustrative example and referring to the schematic pseudo-CT image of FIG. 3, it is possible to compare $\mu_1'+\mu_2'$, i.e. a cumulative attenuation value suggested or predicted by the pseudo-CT values of the pseudo-CT image, with $\mu_1+\mu_2$, i.e. a measured or obtained cumulative attenuation value obtained from the radiation intensity data. Radiation intensity information obtained from a single projection angle can be used as normalisation data with which to calibrate the entire pseudo-CT image. Based on the comparison, the pseudo-CT values can be updated to better reflect the properties of the patient's body. In other words, the estimated attenuation values assigned to each voxel of the pseudo-CT image can be updated based on the obtained radiation intensity data to produce a calibrated, or in other words refined, pseudo-CT image which better reflects the properties of tissue within the patient's body.

As described above, the pseudo-CT image comprises a plurality of voxels, each respective voxel being associated with a pseudo-CT value. The pseudo-CT value can be described as an estimated value which is indicative of an electron density. The calibration therefore can be described as comprising comparing the estimated electron density information in the pseudo-CT image with the obtained electron density information and, based on the comparison, updating each estimated electron density value of the pseudo-CT image to produce a calibrated pseudo-CT image. In other words, the initial pseudo-CT image comprises a plurality of voxels, each respective voxel being associated with a pseudo-CT value. The initial pseudo-CT image can be calibrated by comparing the obtained radiation intensity data with the pseudo-CT values and, based on the comparison, each pseudo-CT value of the pseudo-CT image can be updated to produce the calibrated pseudo-CT image.

To update the pseudo-CT values based on the radiation intensity data, a number of mathematical methods can be used. For example, interpolation methods can be used to update the pseudo-CT values, with the obtained data being used to inform the interpolation method. Similarly, the obtained data can be used to inform one of several possible curve-fitting techniques, with the aim of achieving a 'best-fit' between the cumulative attenuation values determined based on the estimated pseudo-CT values, and the measured cumulative attenuation values determined from the radiation intensity data.

In an example, upon comparing the cumulative attenuation information obtained from the radiation intensity data with the estimated cumulative attenuation information obtained from the pseudo-CT image, it is determined that the pseudo-CT values are on average 5% too low according to the measured data. In a simple example, each pseudo-CT value of the pseudo-CT image can be increased by 5% in order to produce a more accurate, i.e. refined, pseudo-CT image.

In another example, the initial pseudo-CT image is segmented into image regions associated with different tissues or types of tissues, for example, water, bone and air. Each voxel in the pseudo-CT image is thus tagged or labelled with the type of tissue that it is considered to represent. Segmentation techniques, including computer-based segmentation techniques, are well known to the skilled person and will not be discussed further. This information can be factored into the calibration process at step 240 in order to selectively update the pseudo-CT values of the pseudo-CT image according to the type of tissue the particular voxel represents. For example, upon obtaining the radiation intensity data comprising cumulative attenuation information, it can be determined that radiation which has passed primarily through bone tissue has been attenuated to a degree which has a good agreement with the amount of attenuation which would be expected based on the pseudo-CT image. However, radiation which the segmented pseudo-CT image, or the MRI image, indicates has passed through a relatively large amount of soft tissue results in cumulative attenuation information which is less accurate. Using knowledge of the path of the radiation beam, the spatial map of the patient's body provided by the MR data and/or the pseudo-CT image, and image segmentation techniques, it is possible to determine how the pseudo-CT values of the pseudo-CT image should be updated/adjusted based on the type of tissue. In other words, voxels associated with different tissue types can be updated according to the type of tissue they represent, and thus disclosed methods allow the pseudo-CT image to be updated based on different tissue types within a patient's body.

This is particularly useful for lung tissue. A particular downside of current pseudo-CT techniques is that they are unable to assign accurate pseudo-CT values to lung tissue, in part because lung tissue is inhomogeneous and also because lung tissue does not give a strong MR signal due to the low proton density in the lung. Incorporating segmentation techniques into the method as described above means that, at step 240, more accurate pseudo-CT values can be assigned to voxels which are associated with lung tissue within the patient.

As detailed above, the obtained radiation intensity data allows the accuracy of an existing pseudo-CT image to be improved, while minimising the radiation dose given to the patient. Of course, while reference is made to a 'single' beam, angle or direction, it will be appreciated that a small number of beams can be used while achieving the aim of obtaining radiation intensity data to refine a pseudo-CT image while ensuring the exposure of the patient to radiation is less than would be delivered by a full-CT scan. A more accurate pseudo-CT image is obtained, while the radiation dose given to the patient is far less than would be the case if a full CT-scan were to be administered.

In a second implementation of the disclosed methods, the radiation used to obtain the radiation intensity data at step 230 is the radiation that will be used in the RT treatment. In other words, the treatment beam is used to obtain the radiation intensity data.

The degree to which tissue will attenuate radiation, and correspondingly the tissue's degree of sensitivity to radiation, is dependent on the characteristics of the radiation being applied. In particular, attenuation properties of tissue depend upon the frequency of the applied radiation. If pseudo-CT values are refined based on first radiation having first characteristics, for example X-rays having a first frequency, then the resulting refined pseudo-CT image may not accurately describe how tissues within the patient's body will interact with a treatment beam which has different characteristics than the X-rays. For example, if the treatment beam is at a second, different frequency. Accordingly, refining a pseudo-CT image using radiation intensity data obtained using the treatment beam allows a pseudo-CT image to be produced which better describes how the treatment beam will interact with the patient's body.

As is known to the skilled person, radiotherapy typically involves the application of radiation to the patient from multiple angles in order to build up a particular dose at a target region whilst minimising radiation dose to the surrounding, healthy tissue. The RT treatment may therefore comprise the application of multiple sequential radiation beams, each having different characteristics (e.g. different beam shapes, radiation frequency, intensity, and angle of application). For example, a plurality of therapeutic radiation beams may be applied at different angles and intensities, each beam delivering a particular fraction of a predetermined dose to the target region in accordance with the treatment plan. Radiation is thus delivered to the subject in order to deliver a total, cumulative dose of radiation to the target region from a plurality of therapeutic beams according to a radiotherapy treatment plan.

In the second implementation, treatment may be planned based on the initial, i.e. uncalibrated, pseudo-CT image. In this implementation, the application of a therapeutic radiation beam serves two purposes: one, to deliver a dose of radiation to the target region in accordance with the treatment plan, and two, to be used in order to obtain radiation intensity information which can be used to refine the pseudo-CT image in order to facilitate the planning of the remaining radiotherapy treatment. Having applied the therapeutic radiation beam to the patient, and having obtained the radiation intensity data and delivered a fraction of a predetermined dose according to a treatment plan, the pseudo-CT image can be calibrated or refined using the methods described above in relation to the first implementation, or elsewhere herein.

In an example, this method may comprise starting treatment using a treatment plan created using the initial pseudo-CT image, delivering the first RT beam, obtaining radiation intensity data (e.g. by analysing an image generated from the radiation intensity data), and considering whether the density values acquired from the radiation intensity data match, i.e. fit with, the densities for the same regions in the pseudo CT image. If they don't match or fit with the estimated values of the pseudo-CT value, the values of the pseudo-CT image can be amended. The next treatment beam can then be delivered using the new density values, and the process can be repeated.

Figure 5:
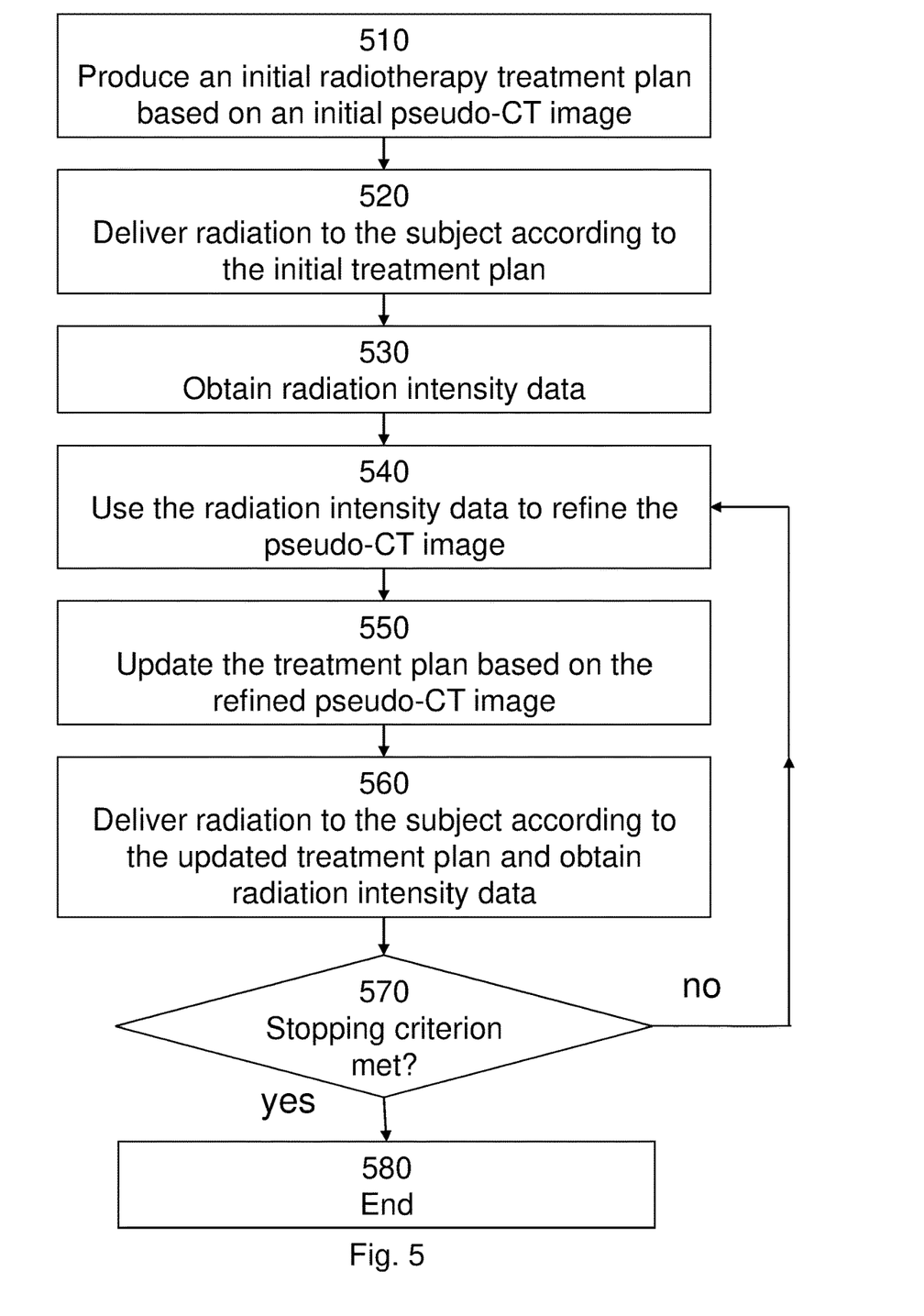
FIG. 5 depicts a flowchart of an iterative process in accordance with the present disclosure.

Taking this example further, in a further disclosed method an iterative process is used to successively refine and improve the accuracy of the pseudo-CT image. The iterative process comprises delivering radiation to the subject according to a treatment plan and updating the treatment plan a plurality of time. Reference is made to FIG. 5, which depicts a flowchart according to an iterative process of the present disclosure.

At step 510, an initial radiotherapy treatment plan is produced based on an initial pseudo-CT image. This process may comprise using the pseudo-CT image to determine an angle, intensity, and method of delivery of a radiation treatment beam. For example, dose calculation algorithms may use the pseudo-CT values of voxels of the pseudo-CT image to determine an optimal angle to apply the radiation. Treatment simulations may be performed using computer software, which may be used to plan the geometric, radiological, and dosimetric aspects of the therapy. The treatment plan may call for radiation comprising a number of different shapes, delivered by beams at different orientations and intensities. The skilled person will be familiar with radiation treatment planning and further details need not be discussed here.

At step 520, radiation is delivered to the subject according to the initial radiotherapy treatment plan. The delivered radiation may be, for example, a single beam at a particular intensity, or having a particular intensity profile, and applied from a particular angle for a predetermined duration. These factors are determined in accordance with the initial treatment plan. The target region receives a dose of radiation, which, depending in part on the accuracy of the initial pseudo-CT image, is equal to the dose of radiation which the initial treatment plan dictates should be applied by the first treatment beam. For example, the delivered dose may be a fraction of the total dose to be delivered to the target region. At step 530, radiation intensity data is obtained. The radiation intensity data is obtained by the radiation detector as the treatment beam is applied to the subject, i.e. as radiation is delivered to the subject.

At step 540, the radiation intensity data is used to refine/calibrate the pseudo-CT image using techniques disclosed herein, and at step 550 the treatment plan is updated based on the refined pseudo-CT image. For example, dose calculation algorithms may use the refined pseudo-CT values to determine the characteristics of the next radiation beam to be applied to the patient. The resulting updated treatment plan is improved, as it is based on a more accurate image of the subject, i.e. a pseudo-CT image comprising more accurate pseudo-CT values. At step 560, radiation is delivered to the patient according to the updated treatment plan. The characteristics of this therapeutic radiation are determined based on a more accurate pseudo-CT image, and are thus better optimised to further minimise radiation dose to healthy tissue. Radiation intensity data is also obtained as the radiation passes through the patient's body.

At step 570, it is determined whether a stopping criterion has been reached. If the stopping criterion has not been reached, then the obtained radiation intensity data is used to refine the pseudo-CT image and steps 540, 550, and 560 are repeated until the stopping criterion is met. When the stopping criterion has been met, the iterative process ends at step 570.

The stopping criterion may take a number of forms. The stopping criterion may be whether or not a predetermined or dynamically determined threshold has been reached. For example, the stopping criterion may be a predetermined number of iterations having been performed. The stopping criterion may be related to, associated with, or based on, the treatment plan. For example, the stopping criterion may comprise determining whether a total cumulative dose has been applied to the target region. The stopping criterion may simply therefore be "is the treatment completed?". The stopping criterion may instead be related to, associated with, or based on, the accuracy of the pseudo-CT values in the pseudo-CT image. For example, determining whether the stopping criterion has been reached may comprise determining that the pseudo-CT values have reached a particular accuracy, or are otherwise sufficiently accurate. For example, the pseudo-CT values may be deemed sufficiently accurate following a determination that the values have not been changed by an amount over a particular percentage amount, either in the previous iteration or over the course of a set number of previous iterations. In this way, the method may comprise determining that the pseudo-CT image is accurate enough for treatment to be optimised, and the pseudo-CT image doesn't need to be refined any further. This iterative method allows treatment to proceed efficiently while ensuring the treatment plan is optimised.

Using the iterative method, the dose applied to the patient by each respective beam of the treatment is constantly being updated based on an increasingly accurate image of the patient. The dose to the patient is not increased over and above existing methods which base RT treatment on pseudo-CT images, as radiation intensity data is obtained from the treatment radiation beams that would have been delivered regardless. In addition, the treatment can become more and more refined and accurate, ensuring the radiation dose to healthy dose is minimised while an optimal dose is delivered to the target region.

In an alternative embodiment, rather than obtaining MR data at step 210 and the pseudo-CT image being specifically produced using e.g. MR imaging apparatus at step 220, the pseudo-CT image may be obtained and/or received in any manner and from any source. Receiving the pseudo-CT may comprise retrieving the pseudo-CT image from the memory. Presently disclosed calibration methods can be used to refine/calibrate any pseudo-CT image, and accordingly the skilled person will appreciate that a method in accordance with the present disclosure can be performed by receiving a pseudo-CT image of at least part of the subject, the pseudo-CT image having been produced based on MR data associated with an MR image of a subject; obtaining radiation intensity data indicative of attenuation properties of tissues within the subject; and producing, using the radiation intensity data to calibrate the pseudo-CT image, a calibrated pseudo-CT image.

In a third implementation of the presently disclosed methods, the radiation intensity data obtained at step 230 may be a coarse CT scan. The coarse CT-scan is not a 'full' or typical CT-scan. Instead, fewer beams and/or fewer projection angle are used. In an example, a 10-beam and low dose MV CBCT image is obtained. The resulting coarse CT image may have a voxel size of approximately 1 $cm^3$, and hence is of a resolution which would render it impractical for use in dosage planning. However, the coarse CT-scan can be used to calibrate the pseudo-CT image, and a substantially smaller radiation dose is applied to the patient than would be applied with a full-CT scan.

In an example, image reconstruction techniques are used following the application of a small number of cone-shaped beams to the patient to build up a reconstructed, coarse CT image. The radiation intensity data in this example may therefore comprise CT projection data. Image reconstruction techniques are used to generate tomographic images from the projection data acquired at different angles around the patient. As known to the skilled person, the type of reconstruction technique used affects image quality and consequently, perhaps the radiation dose which is typically calculated based on a treatment plan based on the image. Typically, it is desirable to achieve the highest possible spatial resolution for a given radiation dose. Suitable reconstruction techniques include techniques which make use of the Feldkamp algorithm, and simultaneous algebraic reconstruction techniques (SART). SART is particularly useful in instances such as the present one, in which limited projection data is available. Various related techniques based on SART may also be used, e.g.: OS-SART, FA-SART, VW-OS-SART, SARTF, etc. These techniques and other reconstruction techniques are generally known to the skilled person.

When the coarse, low resolution CT image is produced, it can be compared to the higher resolution pseudo-CT image in order to improve the accuracy of the pseudo-CT values of the pseudo-CT image.

In a further disclosed method, the pseudo-CT image can be refined based on additional MR data. The MR data is obtained during the radiotherapy treatment, and in some examples the MR data is continuously obtained during treatment. Updating the pseudo-CT image based on MR data taken during the radiotherapy treatment means that the treatment plan can be updated to take into account changes in patient geometry during treatment. This further disclosed method may be performed independently of the other methods and implementations disclosed herein, but may also be combined with, and/or performed alongside, any of the other methods and implementations described herein in order to provide a particularly effective method of refining a pseudo-CT image.

Figure 6:
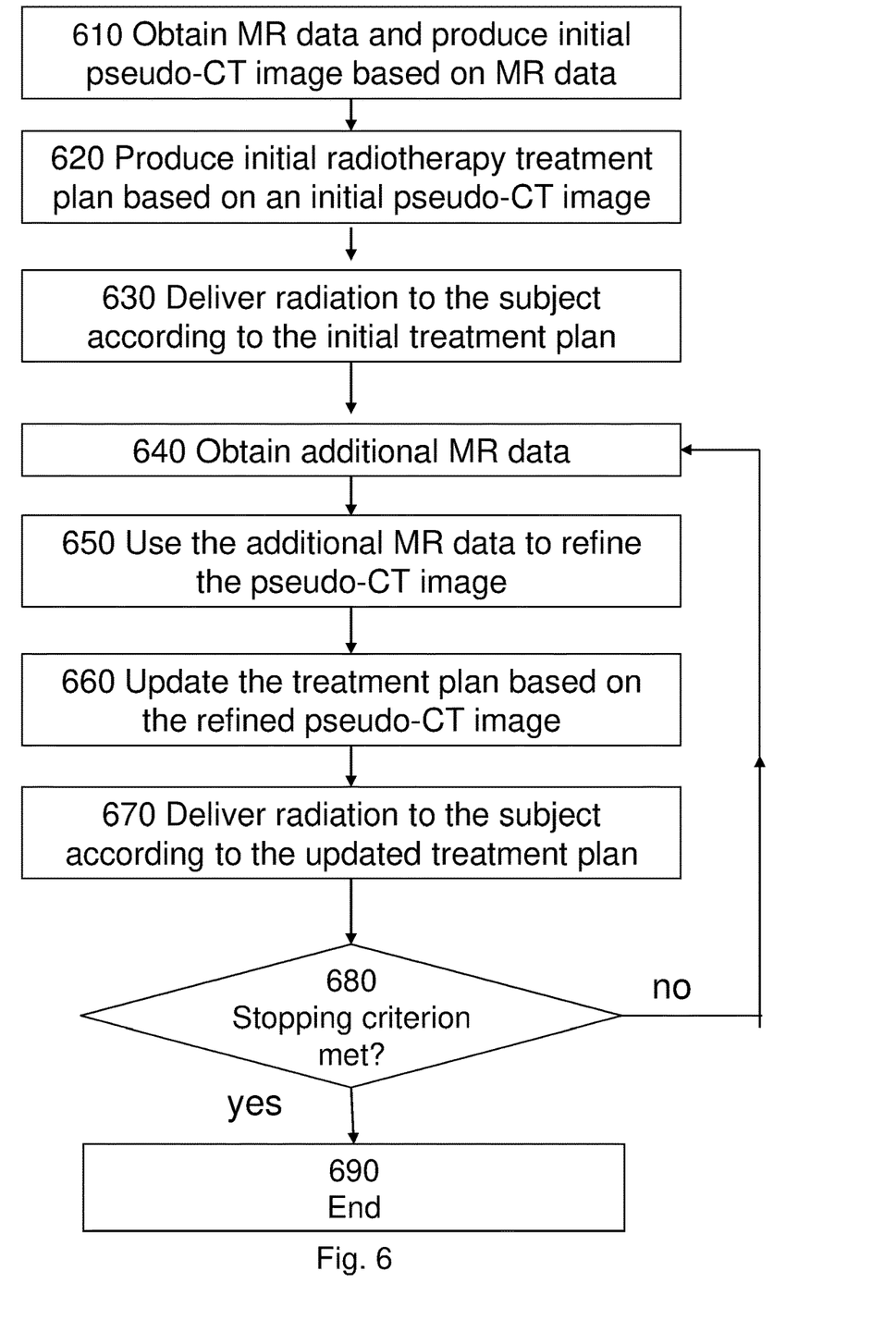
FIG. 6 depicts a flowchart showing an iterative method according to the present disclosure.

FIG. 6 depicts a flowchart showing an iterative method according to the present disclosure. At step 610, MR data is obtained in a manner known to the skilled person and described elsewhere herein. For example, an MR image is taken of the patient. While the initial MR image is obtained, the patient is in an initial position on the patient support surface. In the initial position, for example, the patient's limbs may have an initial orientation, and liquid and gas and other tissues within the patient's body are arranged in a particular manner. A pseudo-CT image is produced based on the MR data using known techniques.

At step 620, an initial radiotherapy treatment plan is produced. The treatment plan is produced at least in part based on the initial pseudo-CT image. For example, the pseudo-CT values may be inputted into dose calculation algorithms in a manner similar or identical to the manner in which this would be done if the pseudo-CT image were in fact a real CT image. At step 630, radiation is delivered to the subject according to the initial treatment plan. As stated elsewhere herein, the initial treatment plan may call for this initial delivery of radiation to comprise an initial treatment beam delivered at a particular angle, with a particular shape, and with a particular frequency and intensity of radiation. This initial delivery of radiation applies a fraction of the total prescribed dose to the target region.

As set out in the background of the present application, in prior methods, CT images are typically used to assist in planning the radiotherapy treatment. However, in prior methods there is necessarily a time delay between obtaining the CT image, planning the treatment, and applying the treatment beam according to the treatment plan. During this time delay, the patient is likely to have moved, meaning that the treatment radiation is being applied according to a pseudo-CT image which is no longer entirely descriptive of the patient's geometry on the support surface at the time of treatment. For example, the patient's limbs may have move to have a different orientation. The patient's movement may comprise conscious movements such as the shifting of weight on the support surface and the slight movement of the patient's limbs for comfort. The patient's movement may also be caused by sub-conscious movements, such as those due to biological processes for example respiration, and the movement of gas and liquid in the body. This may lead to sub-optimal dosages being applied to healthy tissue and the target region as part of the treatment.

At step 640, additional MR data is obtained. For example, an additional MR image is obtained. At step 650, the additional MR data is used to refine the pseudo-CT image. In other words, at this step, the initial pseudo-CT image is refined based on the additional MR data. For example, the geometry of the pseudo-CT image may be adjusted based on the geometry of the additional MR image. In this way, the pseudo-CT image is updated to better reflect the geometry of the patient during treatment, and the radiotherapy treatment is planned based on a more accurate image.

At step 650, the additional MR data is used to refine the pseudo-CT image. This may involve checking that the radiation being delivered to the patient, and the corrections and refinements being applied at, are consistent with the current geometry of the patient. For example, patient respiration will move the ribcage and lung tissues of the patient. This movement may mean that a point in space which had previously been occupied by the patient's lung tissue is now occupied by the patient's ribs.

At step 660, the treatment plan is updated based on the refined pseudo-CT image. For example, the treatment plan is updated to reflect the updated geometry of the patient in the image. At step 670, radiation is delivered to the patient according to the updated treatment plan. For example, the additional MR image may indicate that, compared to the initial MR image used to prepare the initial treatment plan, gas in the patient's lungs or bowel has moved relative to the rest of the patient's body, allowing a more optimal angle to be used for the next treatment beam of the radiotherapy treatment.

At step 680, it is determined whether a stopping criterion has been met. Step 680 may comprise determining whether treatment has stopped. Step 680 is optional, and in some examples steps 640 to step 670 are performed continually until treatment has finished.

If a stopping criterion has been reached, or met, or if it is determined that the iterative process should stop at step 680, then the process ends at block 690.

If the process is to continue, then additional MR data is obtained at step 640, the additional MR data is used to refine the current iteration of the pseudo-CT image at step 650, and the treatment plan is updated based on the updated pseudo-CT image at step 660. Further radiation is delivered to the patient at step 670 based on, i.e. according to, the updated treatment plan.

It will be appreciated that the disclosed method allows a pseudo-CT image and a treatment plan to be dynamically updated as both the patient and, for example, liquid and gas within the patient, move during treatment. In this way, the method ensures that the pseudo-CT accurately describe s the geometry of the patient during treatment. A particular advantage of this method is that the patient's respiration can be taken into account during treatment, allowing the prescribed dose to be delivered more accurately and effectively. As the patient breathes in, gas is brought into the lungs and tissues within the patient are displaced as the lungs expand. The continuously obtained additional MR data allows this change to be tracked, and the changes in tissue location can be accounted for during radiotherapy treatment.

In a particularly advantageous disclosed example, the methods of FIG. 5 and FIG. 6 are combined such that the pseudo-CT values of the pseudo-CT image are continuously refined based on radiation intensity data contained from each treatment beam, and the geometry of the pseudo-CT is continuously updated based on MR data acquired during treatment.

The above implementations and arrangements have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A computer-implemented method for producing a calibrated pseudo-CT image of at least part of a body of a patient for radiation treatment planning, the method comprising:
    obtaining a first pseudo-CT image of at least part of the patient;
    obtaining radiation intensity data indicative of attenuation properties of one or more tissues within the patient; and
    calibrating the first pseudo-CT image of at least part of the patient using the radiation intensity data to produce the calibrated pseudo-CT image.

2. The method of claim 1, wherein the first pseudo-CT image is produced based on MR data, the MR data having been obtained by imaging the patient with an MR imager.

3. The method of claim 2, wherein obtaining the first pseudo-CT image comprises:
    imaging the patient with the MR imager to obtain the MR data.

4. The method of claim 3, wherein the patient is positioned on a patient support surface while the MR data and radiation intensity data are obtained.

5. The method of claim 3, wherein the MR data and radiation intensity data are obtained before the first pseudo-CT image is produced.

6. The method of claim 1, wherein the first pseudo-CT image comprises a plurality of voxels, each respective voxel being associated with a pseudo-CT value, and wherein producing the calibrated pseudo-CT image comprises:
    comparing the obtained radiation intensity data with estimated radiation intensity data, the estimated radiation intensity data being based on at least one of the pseudo-CT values and, based on the comparison of the obtained radiation intensity data with the estimated radiation intensity data, updating each pseudo-CT value of the first pseudo-CT image to produce the calibrated pseudo-CT image.

7. The method of claim 1, further comprising:
    delivering radiation from a radiation source to the patient; and
    obtaining the radiation intensity data from a radiation detector.

8. The method of claim 7, wherein delivering the radiation to the patient further comprises:
    irradiating a target region within the body of the patient to deliver a radiation dose to the target region according to a radiotherapy treatment plan.

9. The method of claim 8, further comprising:
    producing the radiotherapy treatment plan based on the first pseudo-CT image.

10. The method of claim 8, further comprising:
    delivering second radiation to the patient to deliver a second radiation dose to the target region according to a second radiotherapy treatment plan, the second radiotherapy treatment plan being based on the calibrated pseudo-CT image.

11. The method of claim 1, further comprising:
    delivering radiation to the patient according to a treatment plan and updating the treatment plan in an iterative process, each iteration of the iterative process comprising:
    delivering radiation to the patient to deliver a dose of radiation to a target region according to the treatment plan,
    obtaining radiation intensity data indicative of attenuation properties of one or more tissues within the patient; and
    updating the calibrated pseudo-CT image using the radiation intensity data; and
    updating the treatment plan based on the updated calibrated pseudo-CT image.

12. The method of claim 1, wherein the radiation intensity data comprises:
    a calibration CT image of the at least part of the patient, the calibration CT image having a lower resolution than the first pseudo-CT image.

13. The method of claim 1, wherein the first pseudo-CT image comprises one or more of voxels, each respective voxel being associated with a pseudo-CT value and a tissue type; and
    wherein producing the calibrated pseudo-CT image further comprises updating the pseudo-CT values of each voxel based on the radiation intensity data and the tissue type.

14. A non-transitory computer readable medium comprising computer-executable instructions which, when executed by a processor, cause the processor to perform a method for producing a calibrated pseudo-CT image of at least part of a patient for radiation treatment planning, the method comprising:
    obtaining a first pseudo-CT image of at least part of the patient;
    obtaining radiation intensity data indicative of attenuation properties of one or more tissues within the patient; and
    calibrating the first pseudo-CT image of at least part of the patient using the radiation intensity data to produce the calibrated pseudo-CT image.

15. The non-transitory computer readable medium of claim 14, wherein the first pseudo-CT image is produced based on MR data, the MR data having been obtained by imaging the patient with an MR imager.

16. The non-transitory computer readable medium of claim 15, wherein the patient is positioned on a patient support surface while the MR data and radiation intensity data are obtained.

17. The non-transitory computer readable medium of claim 15, wherein the MR data and radiation intensity data are obtained before the first pseudo-CT image is produced.

18. A system for producing a calibrated pseudo-CT image of at least part of a patient for radiation treatment planning, the system comprising:
    a radiation source and a radiation detector, the radiation source for delivering radiation to the patient, and the radiation detector being arranged to detect an intensity of radiation which has passed through the patient;

a controller; and a non-transitory computer readable medium, the computer readable medium comprising computer-executable instructions which, when executed by the controller, cause the system to perform a method for producing a calibrated pseudo-CT image of at least part of a patient for radiation treatment planning, the method comprising:

obtaining a first pseudo-CT image of at least part of the patient;

obtaining radiation intensity data indicative of attenuation properties of tissues within the patient; and calibrating the first pseudo-CT image of at least part of the patient using the radiation intensity data to produce the calibrated pseudo-CT image.

19. The system of claim 18, further comprising an MR imager configured to obtain MR data.

20. The system of claim 19, further comprising:

a patient support surface, wherein the MR imager is configured to obtain the MR data and wherein the radiation detector is configured to detect the intensity of radiation which has passed through the patient while the patient is positioned on the patient support surface.

* * * * *